US008606520B2

(12) United States Patent
Hong et al.

(10) Patent No.: US 8,606,520 B2
(45) Date of Patent: Dec. 10, 2013

(54) SYSTEM AND METHOD FOR DETECTING VOLUMETRIC SOIL WATER CONTENT

(75) Inventors: Sungwook Hong, Bucheon-si (KR); Inchul Shin, Gwangmyeong-si (KR); Mi-Lim Ou, Seoul (KR)

(73) Assignee: Korea Meteorological Administration, Seoul (KR)

( * ) Notice: Subject to any disclaimer, the term of this patent is extended or adjusted under 35 U.S.C. 154(b) by 177 days.

(21) Appl. No.: 13/032,490

(22) Filed: Feb. 22, 2011

(65) Prior Publication Data

US 2011/0307177 A1  Dec. 15, 2011

(30) Foreign Application Priority Data

Mar. 5, 2010  (KR) ........................ 10-2010-0020075

(51) Int. Cl.
*G06F 19/00* (2011.01)
*G01N 22/04* (2006.01)

(52) U.S. Cl.
USPC .............................................. 702/2; 356/627

(58) Field of Classification Search
CPC ................................. G06F 19/00; G01N 22/04
USPC ................... 702/1, 2, 32, 382; 356/600, 627; 382/100, 103, 108, 116; 348/89; 342/1, 342/5, 46, 35 R; 56/10.2 B; 427/457; 505/160; 324/341
See application file for complete search history.

(56) References Cited

U.S. PATENT DOCUMENTS

| 7,728,759 B2 * | 6/2010 | Tillotson et al. ............ 342/26 A |
| 7,739,048 B2 * | 6/2010 | Tillotson et al. .................. 702/3 |
| 2010/0063733 A1 * | 3/2010 | Yunck .......................... 701/213 |

FOREIGN PATENT DOCUMENTS

JP  2004061220 A  *  2/2004

OTHER PUBLICATIONS

Owe, et al., "Surface parameter retrieval at global scales by microwave remote sensing", spie.org, 2003.*
Topp, et al., "The measurement of soil water content using a portable TDR hand probe", Can. J. Soil Sci. 64: 313-321 (Aug. 1984).*
Wigneron, et al., "Retrieving near-surface soil moisture form microwave radiometric observations: current status and future plans", remote Sensing of Envioronment, 85 (2003), 489-506.*
Liu, et al., "Soil moisture retrieval from WindSat using the signle channel algorithm toward a blended global soil moisture product from multiple", Proc. of SPIE vol. 7085, 708501, (2008).*
Blindlish, et al. "Soil moisture mapping and AMSR-E validation using the PSR in SMEX02", Remote Sensing of Environment 103 (2006), 127-139.*
S. Hong, et al., "Soil moisture retrieval in passive microwave remote sensing: a physically based inversion algorithm", 90th AMS Annual Meeting, Thursday, Jan. 21, 2010.*
S. Hong, "Retrieval of refractive index over specular surfaces for remote sensing applications", J. Applied Remote Sensing, vol. 3, 033560 (Oct. 29, 2009).*

* cited by examiner

*Primary Examiner* — Jonathan C Teixeira Moffat
*Assistant Examiner* — Ruihua Zhang
(74) *Attorney, Agent, or Firm* — Seed IP Law Group PLLC

(57) ABSTRACT

The present invention relates to a method that obtains emissivity or reflectivity based on ratios of the brightness temperature measured by a satellite and the land surface temperature, calculates two reflectivity using polarizing features of a microwave according to surface characteristics, and measures a volumetric soil water content of a land surface considering that water has different physical characteristics from those of soil. In particular, it may be possible to measure volumetric soil water contents on territories of other countries as well as regions which have many limitations and troubles in direct measurement of the volumetric soil water contents. Accordingly, valuable materials in terms of nation economy may be produced together with substantial contribution to industrial fields that have direct effects on agriculture and disaster prevention.

9 Claims, 2 Drawing Sheets

SYSTEM AND METHOD FOR DETECTING VOLUMETRIC SOIL WATER CONTENT

BACKGROUND OF THE INVENTION

1. Technical Field

The present invention relates to a system and method of measuring a volumetric soil water content using a satellite.

2. Discussion of the Related Art

Volumetric soil water content is a meteorological factor that is necessary for various applications, such as agriculture, flood, drought, rainfall, or sluices, and the volumetric soil water content is closely related to human lives. Basically, the volumetric soil water content is measured based on a difference in dielectric constant that is a physical characteristic of water and soil. For measurement of volumetric soil water contents, a microwave whose frequency ranges from 1 to 10 GHz is used. Since 1970s, various measurement methods have been suggested with their own advantages and disadvantages, which led to a dispute in terms of verification. The measurement may be performed through an airplane. However, a satellite measurement method is the only method that may show a variation tendency of the volumetric soil water content through the overall measurement. An actual direct measurement has a number of difficulties in various aspects. Accordingly, there is a need for an efficient, satellite-based measurement technology.

SUMMARY OF THE INVENTION

The present invention has been designed to solve the above problems, and embodiments of the present invention provide a system and method of being able to provide useful materials for various applications, such as weather forecast, agriculture, drought, flood, disaster prevention, or the like, by measuring a volumetric soil water content of a land surface using polarizing characteristics of an electromagnetic wave based on materials from a satellite.

According to an embodiment of the present invention, there is provided a system of measuring a volumetric soil water content comprising a non-polarizing reflectivity calculating unit that determines reflectivity R of a soil area using information measured by a measuring sensor of a satellite, a roughness calculating unit that calculates roughness using horizontal and vertical components of the reflectivity provided by the non-polarizing reflectivity calculating unit and corrects the reflectivity to determine corrected reflectivity, a dielectric constant determining unit that determines a dielectric constant from the corrected reflectivity, and a soil water measuring unit that estimates a volumetric soil water content from the dielectric constant.

The non-polarizing reflectivity calculating unit determines horizontal or vertical reflectivity of a land surface using a brightness temperature measured by the measuring sensor of the satellite and a land surface temperature determined by Equation 1:

$$T_S = 0.861 T_{B,37\ GHz,V} + 52.550 \quad \text{[Equation 1]}$$

where, Ts is a land surface temperature, and $T_{B,37\ GHz}$ is a brightness temperature measured by microwave channel 37 GHz from AMSR-E of the AQUA satellite.

The horizontal or vertical reflectivity of the land surface is determined by Equation 2:

$$R \approx 1 - \frac{T_B}{T_S} \quad \text{[Equation 2]}$$

where, R is reflectivity, $T_B$ is a brightness temperature as measured, and $T_S$ is a land surface temperature.

The roughness calculating unit determines reflectivity $R_R$ of a rough surface of soil only that is obtained by excluding a contribution of vegetation to the reflectivity from the reflectivity R using Equation 3:

$$R_R \approx \frac{R}{\Gamma^2} = \left(1 - \frac{T_B}{T_s}\right)\frac{1}{\Gamma^2} \quad \text{[Equation 3]}$$

where, R is reflectivity, $T_B$ is a brightness temperature as measured, $T_S$ is a land surface temperature, and ($\Gamma$) is a transmittance of the vegetation, and determines corrected reflectivity obtained by correcting roughness of the soil using Equation 6:

$$R_{R,V,H} = R_{S,V,H} \times \exp\left[-\left(\frac{4\pi\sigma\cos\theta}{\lambda}\right)^2\right] \quad \text{[Equation 6]}$$

where, $\sigma$ refers to roughness of soil surface, $R_S$ refers to being specular, Rv refers to vertical reflectivity, $R_H$ refers to horizontal reflectivity, $\theta$ refers to a satellite zenithal angle, and $\lambda$ refers to a wavelength of the measurement channel.

The dielectric constant determining unit determines a dielectric constant and determines a volumetric soil water content using the dielectric constant, wherein the volumetric soil water content is determined by Equation 7:

$$M_v = 4.3\times10^{-6}\in_r^3 - 5.5\times10^{-4}\in_r^2 + 2.92\times10^{-2}\in_r - 5.3\times10^{-2} \quad \text{[Equation 7]}$$

where, $\in_r$ is a dielectric constant, Mv is a volumetric soil water content.

According to an embodiment of the present invention, there is provided a method of measuring a volumetric soil water content comprising a first step of determining per-polarizing component reflectivity for each measurement channel using the brightness temperature measured by the measuring sensor of the satellite and the land surface temperature, a second step of calculating roughness of the soil based on the reflectivity R and correcting the reflectivity to produce corrected reflectivity, and a third step of determining a dielectric constant using the corrected reflectivity and estimating the volumetric soil water content.

The reflectivity R in the first step is calculated by Equation 2. The corrected reflectivity in the second step satisfies Equation 6. The dielectric constant in the third step satisfies Equation 7.

According to an embodiment of the present invention, there is provided a recording medium readable by a computer, wherein the recording medium includes a program of executing the system or method.

The embodiments of the present invention provide a system and method of being able to provide useful materials for various applications, such as weather forecast, agriculture, drought, flood, disaster prevention, or the like, by measuring a volumetric soil water content of a land surface using polarizing characteristics of an electromagnetic wave based on materials from a satellite. In particular, according to the embodiments of the present invention, volumetric soil water contents of broad ranges may be known based on the measurement by the satellite, and thus, may be utilized for various applications, such as weather forecast, agriculture, drought, flood, disaster prevention, or the like. For example, the materials may be used as input materials for numerical models used for weather forecast. Also, how dry an area is may be known, and this helps for forecast of yellow dust.

BRIEF DESCRIPTION OF THE DRAWINGS

The embodiments of the present invention will become readily apparent by reference to the following detailed description when considered in conjunction with the accompanying drawings wherein.

DESCRIPTION OF THE EMBODIMENTS

Figure 1:
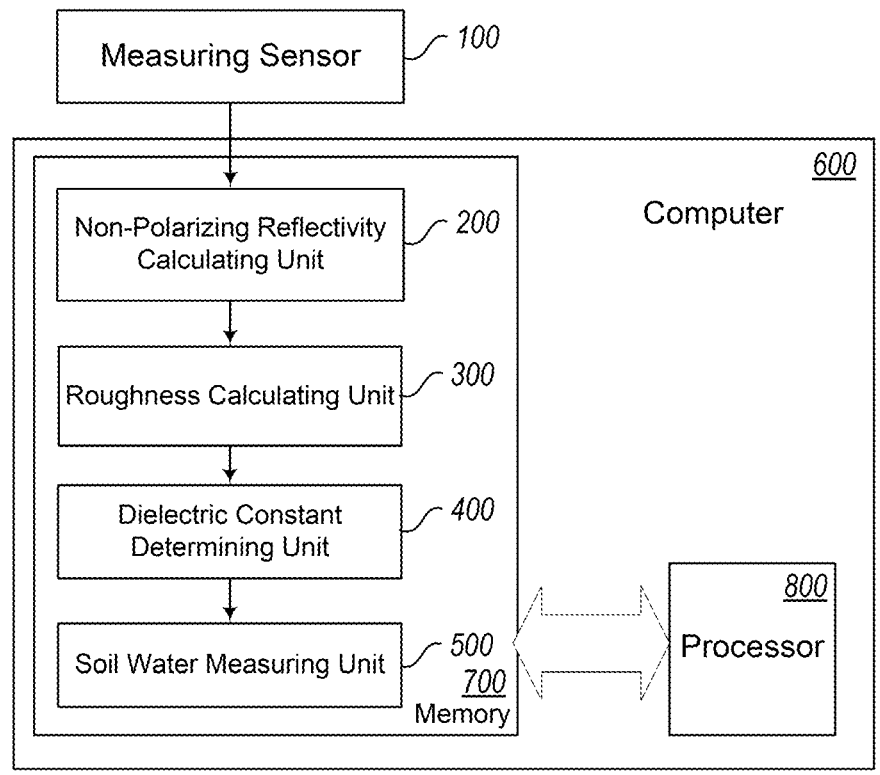
FIG. 1 is a view illustrating a configuration of a system according to an embodiment of the present invention.

Hereinafter, constructions and operations according to an embodiment of the present invention will be described, wherein the same reference numerals are used to denote the same elements and description thereof will not be repeated. The terms "first" and "second" may be used to describe various elements, but the elements should not be limited thereto. The terms are used only to distinguish one element from another element.

Figure 2:
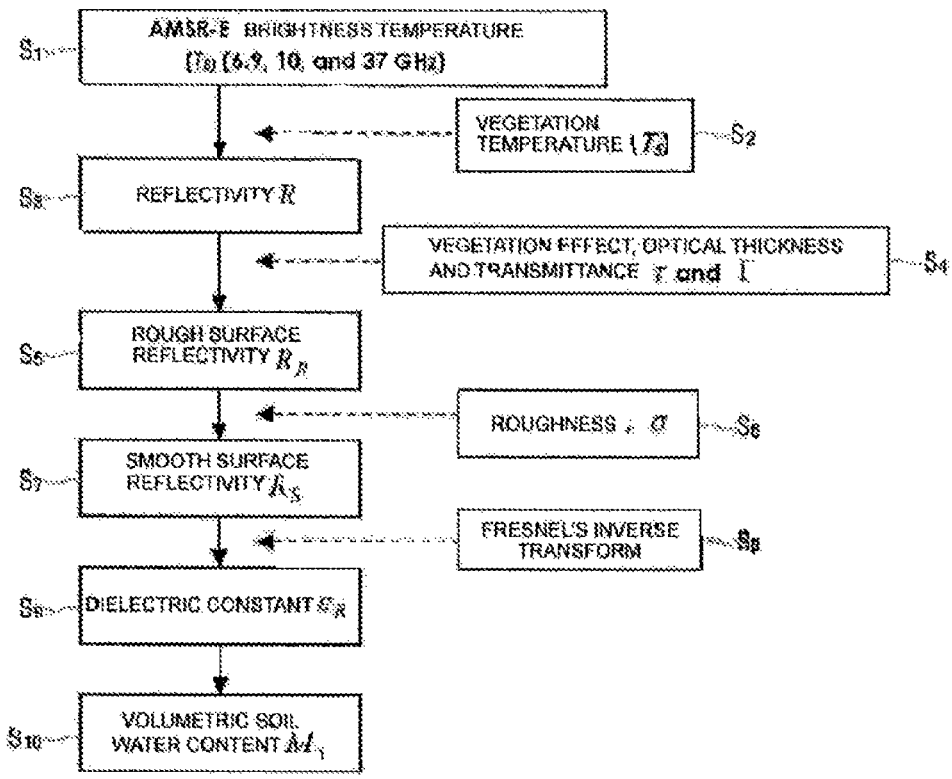
FIG. 2 is a flowchart illustrating a method of measuring a volumetric soil water content using a system according to an embodiment of the present invention.

According to an embodiment of the present invention, there is provided a system and method of measuring a volumetric soil water content that obtains emissivity or reflectivity based on ratios of the brightness temperature measured by a satellite and the land surface temperature, calculates two reflectivity using polarizing features of a microwave according to surface characteristics, and measures a volumetric soil water content of a land surface considering that water has different physical characteristics from those of soil. FIG. 1 is a view schematically illustrating a configuration of a system of measuring a volumetric soil water content (hereinafter, referred to as "system") according to an embodiment of the present invention, and FIG. 2 is a flowchart illustrating operations of components in a system according to an embodiment of the present invention.

The system includes a non-polarizing reflectivity calculating unit 200 that determines reflectivity R of a soil area using information measured by a measuring sensor 100 of a satellite, a roughness calculating unit 300 that calculates roughness using horizontal and vertical components of the reflectivity provided by the non-polarizing reflectivity calculating unit 200 and corrects the reflectivity to determine corrected reflectivity, a dielectric constant determining unit 400 that determines a dielectric constant from the corrected reflectivity, and a soil water measuring unit 500 that estimates a volumetric soil water content from the dielectric constant.

As the information measured by the measuring sensor 100, various satellite materials may be used. Materials measured by a microwave sensor that is called "AMSR-E" and included in an American polar orbital satellite, AQUA, may be generally used. In particular, 6.9 GHz or 10 GHz channel may be used as a measurement channel. According to an embodiment of the present invention, an example will be described that uses satellite image materials associated with a 37 GHz brightness temperature.

The non-polarizing reflectivity calculating unit 200 calculates reflectivity using the brightness temperature measured by the measuring sensor 100 of the satellite and land surface temperature.

It is difficult to directly measure the land surface temperature of a broad area and an area which is not easy to approach, and thus, an empirical equation, such as Equation 1, is employed. Equation 1 is typically used in the field of researching the sea ice temperature.

$$T_S = 0.861 T_{B,37\ GHz,V} + 52.550 \quad \text{[Equation 1]}$$

where, Ts is a land surface temperature, and $T_{B,37\ GHz}$ is a brightness temperature measured by microwave channel 37 GHz from AMSR-E of the AQUA satellite.

Reflectivity R may be calculated from Equation 2 using the land surface temperature and the brightness temperature. Because the atmospheric effect on reflectivity R may be disregarded at frequencies of 10 GHz or less, Equation 2 may be used. The method using Equation 2 is provided by NASA (National Aeronautics and Space Administration). Reflectivity R is calculated as a ratio of the land surface temperature and the brightness temperature.

$$R \approx 1 - \frac{T_B}{T_S} \quad \text{[Equation 2]}$$

where, R is reflectivity, $T_B$ is a brightness temperature as measured, and $T_S$ is a land surface temperature.

The roughness calculating unit 300 calculates roughness using horizontal and vertical components of the reflectivity, which are also referred to as "horizontal reflectivity and vertical reflectivity" throughout the specification and the drawings, provided by the non-polarizing reflectivity calculating unit 200 and corrects the reflectivity to determine corrected reflectivity.

Specifically, according to a radioactive transfer equation, the measured brightness temperature varies with the land surface temperature, atmospheric transmittance, vegetation, scattering rate, etc. It is largely assumed according to previous research results that the scattering rate is very low in a frequency range of 10 GHz or less, and the vegetation temperature is similar to the land surface temperature. Accordingly, reflectivity $R_R$ of rough surface of soil only, which is also referred to as "rough surface reflectivity" throughout the specification and the drawings, is obtained, wherein a contribution of the vegetation to the reflectivity is excluded from the reflectivity R.

$$R_R \approx \frac{R}{\Gamma^2} = \left(1 - \frac{T_B}{T_S}\right)\frac{1}{\Gamma^2} \quad \text{[Equation 3]}$$

wherein R is reflectivity, $T_B$ is a brightness temperature as measured, $T_S$ is a land surface temperature, and $\Gamma$ is a transmittance of the vegetation.

The transmittance of the vegetation may be obtained by calculating an optical thickness ($\tau$) using a microwave polarization difference index.

Thereafter, the rough surface reflectivity $R_R$ is converted to specular reflectivity in Equation 6, by first correcting surface roughness using Equation 4 that is referred to as the Hong approximation and uses polarizing characteristics of electromagnetic waves and Equation 5.

$$R_{s,H} = R_{s,V}^{\cos^2\theta} \quad \text{[Equation 4]}$$

wherein S refers to specular reflection, V refers to vertical polarization, H refers to horizontal polarization, and θ refers to a zenithal angle of the satellite. The roughness σ is measured by Equation 5 using non-polarized reflectivity, which includes a wavelength λ of the measurement channel, the satellite zenithal angle θ, and vertical reflectivity $R_V$ and horizontal reflectivity $R_H$.

$$\sigma = \frac{\lambda}{4\pi\cos\theta} \cdot \sqrt{\ln\left(\frac{R_{s,V}^{\cos^2\theta}}{R_{s,H}}\right)} \quad \text{[Equation 5]}$$

Then, specular reflectivity of soil as obtained by correcting the roughness may be expressed as Equation 6.

$$R_{R,V,H} = R_{S,V,H} \times \exp\left[-\left(\frac{4\pi\sigma\cos\theta}{\lambda}\right)^2\right] \quad \text{[Equation 6]}$$

where, σ refers to roughness of soil surface, $R_S$ refers to being specular, Rv refers to vertical reflectivity, $R_H$ refers to horizontal reflectivity, θ refers to a satellite zenithal angle, and λ refers to a wavelength of the measurement channel.

Accordingly, a dielectric constant $\in_r$ may be obtained by performing Fresnel's inverse transform on the vertical reflectivity and horizontal reflectivity. A volumetric soil water content Mv is obtained based on an empirical equation or experimental equation between the obtained dielectric constant $\in_r$ and the volumetric soil water content Mv. Equation 7 shows a relationship between the dielectric constant and the volumetric soil water content.

$$M_v = 4.3 \times 10^{-6} \in_r^3 - 5.5 \times 10^{-4} \in_r^2 + 2.92 \times 10^{-2} \in_r - 5.3 \times 10^{-2} \quad \text{[Equation 7]}$$

where, $\in_r$ is a dielectric constant, Mv is a volumetric soil water content.

Summarizing the constructions and operations of the system with reference to FIGS. 1 and 2, brightness temperature for each polarizing component, which is measured by the microwave measuring sensor of the satellite, and the land surface temperature are used to calculate reflectivity for each polarizing component. The reflectivity for each polarizing component varies with materials, and thus, the volumetric soil water content may be calculated by using a comparison in dielectric constant between water and soil.

More specifically, the volumetric soil water content may be measured by a method including the following steps using the system according to an embodiment of the present invention.

The method may include a first step of determining per-polarizing component reflectivity for each measurement channel using the brightness temperature measured by the measuring sensor of the satellite and the land surface temperature, a second step of calculating roughness of the soil based on the reflectivity R and correcting the reflectivity to produce corrected reflectivity, and a third step of determining a dielectric constant using the corrected reflectivity and estimating the volumetric soil water content.

In the first step of determining the reflectivity, vertical and horizontal reflectivity components may be calculated based on the brightness temperature measured by a microwave channel for each satellite zenithal angle, for example, 6.9 GHz channel and the land surface temperature calculated by Equation 1. In this case, the vertical and horizontal reflectivity components may be calculated using Equation 2.

Further, the reflectivity R may be represented as reflectivity $R_R$ of rough surface of the soil, which is obtained by excluding the contribution of vegetation from the reflectivity R, by using Equation 3. Thereafter, to convert the rough surface reflectivity $R_R$ to the specular reflectivity, Equations 4 and 5 may be used that produce corrected reflectivity of specular surface (soil surface) as obtained by correcting the rough surface. The resultant equation may be represented as Equation 6.

Thereafter, the dielectric constant may be yielded by performing Fresnel's inverse transform on the vertical reflectivity and horizontal reflectivity.

Figures 3, 4:
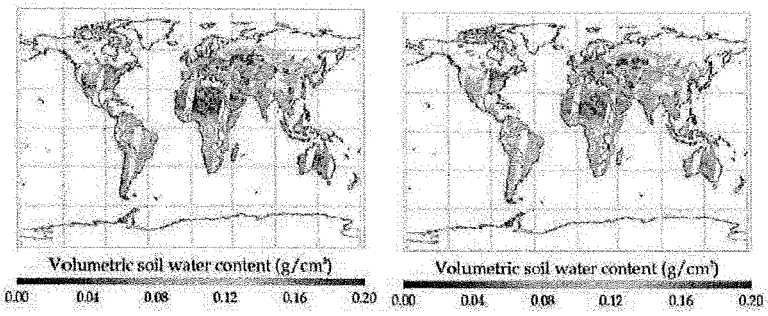
FIG. 3 illustrates results of volumetric soil water contents measured by a system and method according to an embodiment of the present invention and verified results.
FIG. 4 is a view illustrating an example of implementing a system in software according to an embodiment of the present invention.

FIG. 3 illustrates an example obtained by actual application of the system, wherein volumetric soil water contents are shown as obtained by using the American polar orbital satellite, AQUA, and the method according to an embodiment of the present invention.

Specifically, the volumetric soil water contents were calculated by the above method using the AQUA, and subjected to indirect verification. The date was Apr. 1, 2009. A desert, such as the Sahara desert, exhibited a low volumetric soil water content, and regions, such as Amazon areas or African continent, exhibited a high volumetric soil water content. The left view illustrates results obtained by using 6.9 GHz channel, and the right view illustrates results obtained by using 10 GHz channel. The results from the two views nearly conform to each other (wherein, a comparison with actual operation results from NASA in the U.S. and JAXA in Japan was made for verification, and quantitatively and qualitatively proper results were obtained).

According to an embodiment of the present invention, the volumetric soil water contents could be provided based on the brightness temperature directly measured by the satellite without relying on the forward model and assumption that as little water as possible exists on the land surface.

That is, emissivity or reflectivity is obtained based on ratios of the brightness temperature measured by a satellite and the land surface temperature, two reflectivity are calculated using polarizing features of a microwave according to surface characteristics, and a volumetric soil water content of a land surface is measured considering that water has different physical characteristics from those of soil. In particular, it may be possible to measure volumetric soil water contents on territories of other countries as well as regions which have many limitations and troubles in direct measurement of the volumetric soil water contents. Accordingly, valuable materials in terms of nation economy may be produced together with substantial contribution to industrial fields that have direct effects on agriculture and disaster prevention.

FIG. 4 illustrates an example of implementing in software a volumetric soil water content measuring system according to an embodiment of the present invention. Each of the components included in the above system according to an embodiment of the present invention may be implemented in software. For example, the non-polarizing reflectivity calculating unit 200 that determines reflectivity R of a soil area using information measured by the measuring sensor 100 of a satellite, the roughness calculating unit 300 that calculates roughness using horizontal and vertical components of the reflectivity provided by the non-polarizing reflectivity calculating unit 200 and corrects the reflectivity to determine corrected reflectivity, the dielectric constant determining unit 400 that determines a dielectric constant from the corrected reflectivity, and the soil water measuring unit 500 that estimates a volumetric soil water content from the dielectric constant, respectively, may be realized as software modules.

Further, when the system and method are implemented according to an embodiment of the present invention, instructions may be recorded in a computer-readable medium that may be read by a computer 600 having a memory 700 and a processor 800 programmed to execute the instructions.

The invention has been explained above with reference to exemplary embodiments. It will be evident to those skilled in the art that various modifications may be made thereto without departing from the broader spirit and scope of the invention. Further, although the invention has been described in the context its implementation in particular environments and for particular applications, those skilled in the art will recognize that the present invention's usefulness is not limited thereto and that the invention can be beneficially utilized in any number of environments and implementations. The foregoing description and drawings are, accordingly, to be regarded in an illustrative rather than a restrictive sense.

What is claimed is:

1. A system of measuring a volumetric soil water content, the system comprising:
    a non-polarizing reflectivity calculating unit that determines reflectivity R of a soil area using information measured by a measuring sensor of a satellite;
    a roughness calculating unit that corrects the reflectivity R using a calculated roughness to determine a corrected reflectivity;
    a dielectric constant determining unit that determines a dielectric constant from the corrected reflectivity; and
    a soil water measuring unit that estimates a volumetric soil water content from the dielectric constant;
    wherein reflectivity of a rough surface ($R_R$), which is obtained by using the reflectivity R, is converted into specular reflectivity ($R_s$) using Equation 6:

$$R_{R,V,H} = R_{S,V,H} \times \exp\left[-\left(\frac{4\pi\sigma\cos\theta}{\lambda}\right)^2\right], \quad [\text{Equation 6}]$$

wherein S is specular reflection, V is vertical polarization, H is horizontal polarization, and $\theta$ is a satellite zenithal angle, and wherein the roughness ($\sigma$) is calculated by applying reflectivity of the rough surface ($R_R$) into Equation 5:

$$\sigma \approx \frac{\lambda}{4\pi\cos\theta} \cdot \sqrt{\ln\left(\frac{R_{R,V}^{\cos^2\theta}}{R_{R,H}}\right)}, \quad [\text{Equation 5}]$$

wherein $\lambda$ is a wavelength of the measurement channel, $\theta$ is a satellite zenithal angle, $R_v$ is a vertical reflectivity, and $R_H$ is a horizontal reflectivity.

2. The system of claim 1, wherein the non-polarizing reflectivity calculating unit determines a land surface temperature by applying a brightness temperature measured by the measuring sensor of the satellite into Equation 1:

$$T_S = 0.861 T_{B,37\ GHz,V} + 52.550 \quad [\text{Equation 1}]$$

wherein Ts is a land surface temperature, and $T_{B,37\ GHz}$ is a brightness temperature measured by a microwave channel of the satellite at a frequency of 37 GHz.

3. The system of claim 2, wherein the non-polarizing reflectivity calculating unit determines the reflectivity R by applying the brightness temperature and the land surface temperature into Equation 2 below:

$$R \approx 1 - \frac{T_B}{T_S} \quad [\text{Equation 2}]$$

wherein R is reflectivity, $T_B$ is a brightness temperature as measured, and $T_S$ is a land surface temperature.

4. The system of claim 3, wherein the roughness calculating unit determines reflectivity $R_R$ of a rough surface of soil only that is obtained by excluding a contribution of vegetation to the reflectivity from the reflectivity R using Equation 3:

$$R_R \approx \frac{R}{\Gamma^2} = \left(1 - \frac{T_B}{T_S}\right)\frac{1}{\Gamma^2} \quad [\text{Equation 3}]$$

where, R is reflectivity, $T_B$ is a brightness temperature as measured, $T_S$ is a land surface temperature, and ($\Gamma$) is a transmittance of the vegetation, and determines corrected reflectivity obtained by correcting roughness of the soil using Equation 6:

$$R_{R,V,H} = R_{S,V,H} \times \exp\left[-\left(\frac{4\pi\sigma\cos\theta}{\lambda}\right)^2\right] \quad [\text{Equation 6}]$$

where, $\sigma$ refers to roughness of soil surface, $R_S$ refers to being specular, $R_v$ refers to vertical reflectivity, $R_H$ refers to horizontal reflectivity, $\theta$ refers to a satellite zenithal angle, and $\lambda$ refers to a wavelength of the measurement channel.

5. The system of claim 4, wherein the dielectric constant determining unit determines a dielectric constant and determines a volumetric soil water content using the dielectric constant, wherein the volumetric soil water content is determined by Equation 7:

$$M_v = 4.3 \times 10^{-6} \in_r^3 - 5.5 \times 10^{-4} \in_r^2 + 2.92 \times 10^{-2} \in_r - 5.5 \times 10^{-2} \quad [\text{Equation 7}]$$

where, $\in_r$ is a dielectric constant, Mv is a volumetric soil water content.

6. A method of measuring a volumetric soil water content by a system of measuring a volumetric soil water content, the method comprising:
    by the system of measuring a volumetric soil water content, a first step of determining a reflectivity R using a brightness temperature measured by a measuring sensor of a satellite and a land surface temperature;
    by a system of measuring a volumetric soil water content, a second step of correcting the reflectivity R using a calculated roughness to determine a corrected reflectivity; and
    wherein reflectivity ($R_R$) of a rough surface, which is obtained by using the reflectivity R, is converted into specular reflectivity ($R_s$) using Equation 6:

$$R_{R,V,H} = R_{S,V,H} \times \exp\left[-\left(\frac{4\pi\sigma\cos\theta}{\lambda}\right)^2\right], \quad [\text{Equation 6}]$$

wherein S is specular, V is a vertical polarization, H is horizontal polarization, and $\theta$ is a satellite zenithal angle), and wherein the roughness ($\sigma$) is calculated by applying reflectivity ($R_R$) of the rough surface into Equation 5:

$$\sigma = \frac{\lambda}{4\pi\cos\theta} \cdot \sqrt{\ln\left(\frac{R_{s,V}^{\cos^2\theta}}{R_{s,H}}\right)} \quad \text{[Equation 5]}$$

wherein λ is a wavelength of the measurement channel, θ is a satellite zenithal angle, $R_v$ is a vertical reflectivity, and $R_H$ is a horizontal reflectivity); and by the system of measuring a volumetric soil water content, a third step of determining a dielectric constant using the corrected reflectivity and estimating the volumetric soil water content.

7. The method of claim 6, wherein the reflectivity R in the first step is calculated by Equation 2:

$$R \approx 1 - \frac{T_B}{T_S} \quad \text{[Equation 2]}$$

where, R is reflectivity, $T_B$ is a brightness temperature as measured, and $T_S$ is a land surface temperature.

8. The method of claim wherein the dielectric constant in the third step satisfies Equation 7:

$$M_v = 4.3 \times 10^{-6} \in_r^3 - 5.5 \times 10^{-4} \in_r^2 + 2.92 \times 10^{-2} \in_r - 5.3 \times 10^{-2} \quad \text{[Equation 7]}$$

where, $\in_r$ is a dielectric constant, Mv is a volumetric soil water content.

9. One or more non-transitory computer readable storage media storing computer-executable instructions which, when executed by a computer, cause the computer to:

determine reflectivity R using a brightness temperature measured by a measuring sensor of a satellite and a land surface temperature;

correct the reflectivity R using a calculated roughness; and determine a dielectric constant using the corrected reflectivity; and estimate the volumetric soil water content from the dielectric constant;

wherein reflectivity ($R_R$) of a rough surface, which is obtained by using the reflectivity R, is converted into specular reflectivity ($R_s$) using Equation 6:

$$R_{R,V,H} = R_{S,V,H} \times \exp\left[-\left(\frac{4\pi\sigma\cos\theta}{\lambda}\right)^2\right] \quad \text{[Equation 6]}$$

wherein S is specular, V is a vertical polarization, H is a horizontal polarization, and θ is a satellite zenithal angle), and wherein the roughness (σ) is calculated by applying reflectivity ($R_R$) of the rough surface into Equation 5:

$$\sigma \approx \frac{\lambda}{4\pi\cos\theta} \cdot \sqrt{\ln\left(\frac{R_{R,V}^{\cos^2\theta}}{R_{R,H}}\right)}, \quad \text{[Equation 5]}$$

wherein λ is a wavelength of the measuring sensor, θ is a satellite zenithal angle, $R_R$ is a vertical reflectivity, and $R_H$ is a horizontal reflectivity).

* * * * *

UNITED STATES PATENT AND TRADEMARK OFFICE
CERTIFICATE OF CORRECTION

PATENT NO. : 8,606,520 B2
APPLICATION NO. : 13/032490
DATED : December 10, 2013
INVENTOR(S) : Sungwook Hong et al.

Page 1 of 2

It is certified that error appears in the above-identified patent and that said Letters Patent is hereby corrected as shown below:

On the Title Page

Item (56):
"Liu, et al., "Soil moisture retrieval from WindSat using the signle channel algorithm toward a blended global soil moisture product from multiple", Proc. of SPIE vol. 7085, 708501, (2008)." should read, --Liu, et al., "Soil moisture retrieval from WindSat using the single channel algorithm toward a blended global soil moisture product from multiple microwave sensors", Proc. of SPIE vol. 7085, 708501, (2008).--.

In the Claims

Column 7, Line 61:
"wherein Ts is a land surface temperature, and $T_{B,37\ GHz}$ is a" should read, --wherein $T_S$ is a land surface temperature, and $T_{B,37\ GHz}$ is a--.

Column 8, Lines 39-40:
"$M_v=4.3\times10^{-6}\epsilon_r^3-5.5\times10^{-4}\epsilon_r^2+2.92\times10^{-2}\epsilon_r-5.5\times10^{-2}$" should read, --$M_v=4.3\times10^{-6}\epsilon_r^3-5.5\times10^{-4}\epsilon_r^2+2.92\times10^{-2}\epsilon_r-5.3\times10^{-2}$--.

Column 8, line 41:
"where, $\epsilon_r$ is a dielectric constant, Mv is a volumetric soil" should read, --where, $\epsilon_r$ is a dielectric constant, $M_v$ is a volumetric soil--.

Column 8, Lines 64-65:
"horizontal polarization, and Θ is a satellite zenithal angle), and" should read, --horizontal polarization, and Θ is a satellite zenithal angle, and--.

Signed and Sealed this
Thirteenth Day of May, 2014

Michelle K. Lee
*Deputy Director of the United States Patent and Trademark Office*

CERTIFICATE OF CORRECTION (continued)
U.S. Pat. No. 8,606,520 B2

Column 9, Lines 1-5:

" $\sigma \approx \dfrac{\lambda}{4\pi \cos\theta} \cdot \sqrt{\ln\left(\dfrac{R_{S,V}^{\cos^2\theta}}{R_{S,H}}\right)}$ " should read, -- $\sigma = \dfrac{\lambda}{4\pi \cos\theta} \cdot \sqrt{\ln\left(\dfrac{R_{R,V}^{\cos^2\theta}}{R_{R,H}}\right)}$ --.

Column 9, Line 9:
"$R_H$ is a horizontal reflectivity); and" should read, --$R_H$ is a horizontal reflectivity; and--.

Column 9, Line 23:
"8. The method of claim wherein the dielectric constant in" should read, --8. The method of claim 6 wherein the dielectric constant in--.

Column 9, Line 28:
"where, $\epsilon_r$ is a dielectric constant, Mv is a volumetric soil" should read, --where, $\epsilon_r$ is a dielectric constant, $M_v$ is a volumetric soil--.

Column 10, Lines 18-19:
"horizontal polarization, and Θ is a satellite zenithal angle), and" should read, --horizontal polarization, and Θ is a satellite zenithal angle, and--.

Column 10, Line 30:
"satellite zenithal angle, $R_R$ is a vertical reflectivity, and" should read, --satellite zenithal angle, $R_v$ is a vertical reflectivity, and--.

Column 10, Line 31:
"$R_H$ is a horizontal reflectivity)." should read, --$R_H$ is a horizontal reflectivity.--.